(12) United States Patent
Bastiyali

(10) Patent No.: US 12,377,785 B2
(45) Date of Patent: Aug. 5, 2025

(54) SMART SAFE CONSOLE SYSTEM

(71) Applicant: Bastiyali Inventions LLC, New York, NY (US)

(72) Inventor: Tarkan Bastiyali, New York, NY (US)

( * ) Notice: Subject to any disclaimer, the term of this patent is extended or adjusted under 35 U.S.C. 154(b) by 779 days.

(21) Appl. No.: 17/650,354

(22) Filed: Feb. 8, 2022

(65) Prior Publication Data

US 2023/0249624 A1  Aug. 10, 2023

(51) Int. Cl.
*B60R 7/04* (2006.01)
*A61L 2/10* (2006.01)
*B60R 11/02* (2006.01)

(52) U.S. Cl.
CPC .......... *B60R 7/04* (2013.01); *A61L 2/10* (2013.01); *B60R 11/0241* (2013.01); *B60R 11/0252* (2013.01); *A61L 2202/122* (2013.01); *B60R 2011/0294* (2013.01)

(58) Field of Classification Search
CPC .......... B60K 28/08; B60R 7/04; B60R 16/03; B60R 2011/0075; B60R 25/209; B60R 25/22; B60R 25/24; E05B 83/32
See application file for complete search history.

(56) References Cited

U.S. PATENT DOCUMENTS

| | | | |
|---|---|---|---|
| 9,783,124 B2 | 10/2017 | Catlin et al. | |
| 9,900,417 B1 | 2/2018 | Ruiz | |
| 10,011,240 B1 | 7/2018 | Ranganathan et al. | |
| 10,027,795 B1 | 7/2018 | Maguire et al. | |
| 10,440,633 B1 * | 10/2019 | Bastiyali | H04W 48/04 |
| 10,543,799 B1 * | 1/2020 | Werner | B64D 45/0015 |
| 11,931,472 B1 * | 3/2024 | Hong | B60H 3/0078 |
| 12,071,099 B2 | 8/2024 | Bastiyali | |
| 2012/0191616 A1 | 7/2012 | Putman et al. | |
| 2014/0054430 A1 | 2/2014 | Jacobson | |
| 2014/0287709 A1 | 9/2014 | Iwade | |
| 2017/0064056 A1 | 3/2017 | Uhlig et al. | |
| 2019/0077371 A1 | 3/2019 | Gaither | |
| 2019/0143935 A1 | 5/2019 | Flick | |
| 2019/0386513 A1 * | 12/2019 | Bavisi | G06F 21/32 |
| 2021/0222660 A1 | 7/2021 | Gil Vera | |
| 2022/0378957 A1 * | 12/2022 | Hanney | B60R 7/04 |
| 2023/0264655 A1 | 8/2023 | Reber et al. | |

(Continued)

FOREIGN PATENT DOCUMENTS

| | | | | |
|---|---|---|---|---|
| CN | 107103647 A | * | 8/2017 | .......... G01S 5/0027 |
| DE | 102015117559 A1 | * | 4/2016 | .............. A61L 2/10 |
| DE | 102017200711 A1 | * | 7/2018 | |

(Continued)

OTHER PUBLICATIONS

International Search Report including Written Opinion for Application No. PCT/US2024/010847 mailed Feb. 23, 2024. 9 pgs.

*Primary Examiner* — Drew J Brown

(57) ABSTRACT

A smart safe console system is provided herein. The smart safe console system includes a smart safe console assembly for mounting in a vehicle, having a safe body suitable for securing an electronic device, a button configured for controlling input and output to and from the electronic device when a vehicle hosting the smart safe console system is in use, and a wireless charging apparatus. Such smart safe console system is useful for improving the safety of a user when traveling in a vehicle with an electronic device.

18 Claims, 5 Drawing Sheets

(56) References Cited

U.S. PATENT DOCUMENTS

Figure 1:
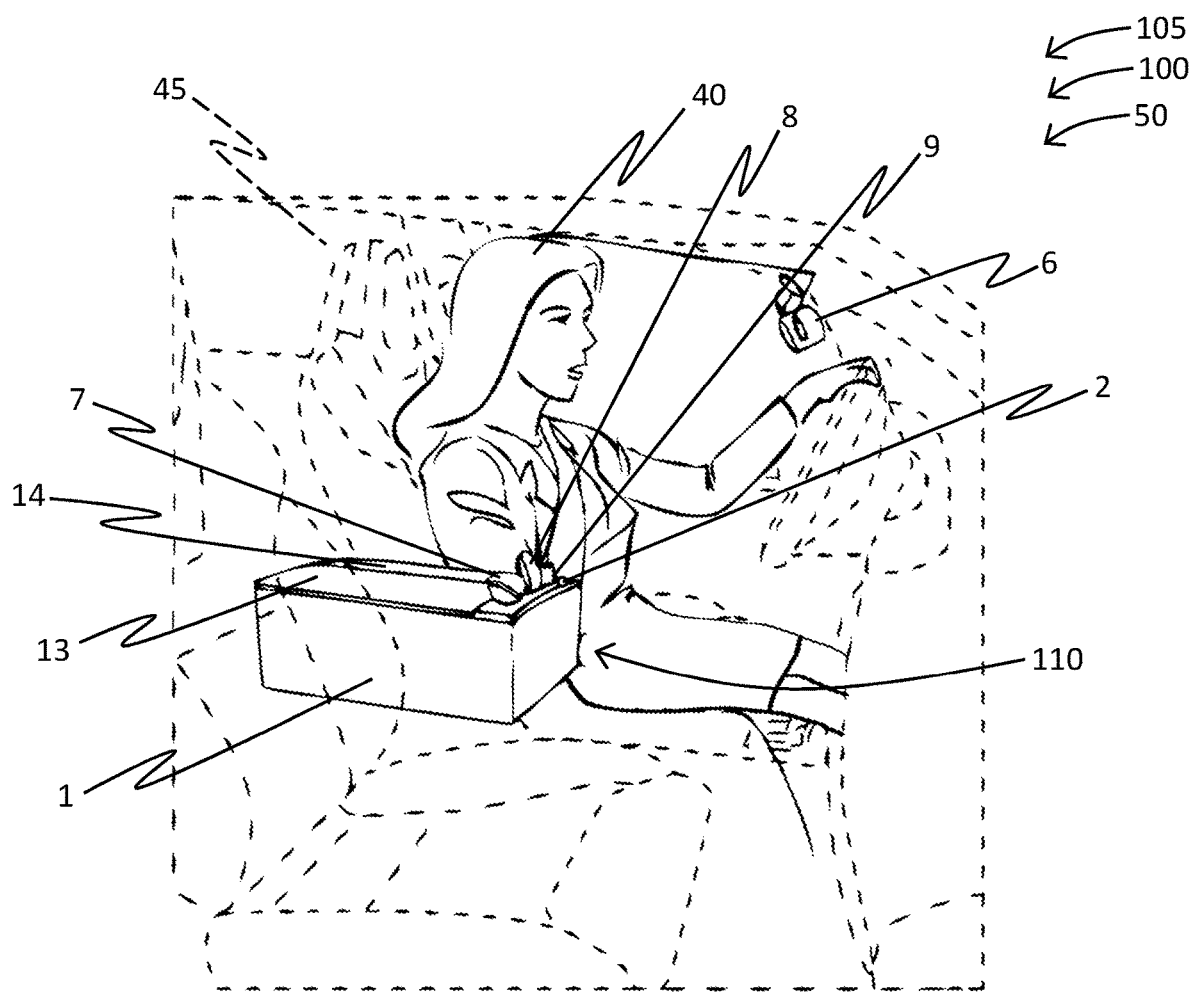
Figure 1:
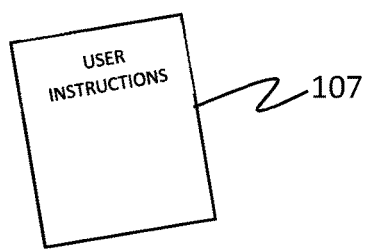

2023/0382406 A1    11/2023    Roberts et al.

FOREIGN PATENT DOCUMENTS

| | | | | |
|---|---|---|---|---|
| DE | 102018211954 A1 | | 3/2019 | |
| DE | 102018219007 A1 | | 11/2019 | |
| DE | 102021004653 A1 | * | 3/2023 | .............. A61L 2/10 |
| EP | 3718818 A1 | | 10/2020 | |
| KR | 20220160751 A | | 12/2022 | |
| KR | 20220170317 A | * | 12/2022 | |
| WO | WO-9922504 A1 | * | 5/1999 | ......... B60R 11/0241 |

* cited by examiner

SMART SAFE CONSOLE SYSTEM

NOTICE OF COPYRIGHTS AND TRADE DRESS

A portion of the disclosure of this patent document contains material which is subject to copyright or trade dress protection. This patent document may show and/or describe matter that is or may become trade dress of the owner. The copyright and trade dress owner has no objection to the facsimile reproduction by anyone of the patent disclosure, as it appears in the Patent and Trademark Office patent files or records, but otherwise reserves all copyright and trade dress rights whatsoever.

CLAIM OF PRIORITY

This application does not claim priority to any patent or patent application.

FIELD OF THE EMBODIMENTS

The present invention relates generally to the field of vehicle safety of existing art and more specifically relates to containment systems for electronic devices.

BACKGROUND

Electronic devices like phones, tablets, smart glasses, and the like are becoming increasingly common in modern times. Such devices can be used for a variety of tasks including messaging, phone conversations, social media, navigation, photography, etc. With so many features offered on electronic devices, many people struggle to stop using the device during necessary times such as operating a vehicle. Many vehicle accidents are a result from distractions caused by electronic devices which is dangerous for public road safety.

Prior attempts to solve this problem include inhibiting all features and communications to and from the electronic device. However, the electronic devices offer a variety of resources that can be useful to a user or operator. Further, family members or friends can become worried when a message or phone call is not returned. Therefore, a suitable solution is required.

SUMMARY OF THE INVENTION

The present disclosure provides a smart safe console system comprising an assembly mounted in a vehicle, the smart safe console system including: a safe body that during vehicle use secures an electronic device against physical access, preferably where the safe body opens and closes, and, when closed, the safe body secures the electronic device against physical access, preferably where the safe body is configured to communicate with the electronic device, when the electronic device is placed within the safe body, preferably where the safe body comprises at least one material with electromagnetic radiation shielding properties, preferably where the safe body comprises at least one material with antiviral properties. In an embodiment, the smart safe console system includes a button that controls input to and output from the electronic device. In an embodiment, the smart safe console system includes a wireless charging apparatus configured to wirelessly charge the electronic device, when the electronic device is placed within the safe body.

In an embodiment, the smart safe console system includes an apparatus configured to emit sanitizing radiation into the interior of the safe body, when the safe body is closed. In some embodiments, the emitted sanitizing radiation is ultraviolet radiation sufficient to inactivate or destroy one or more types of viruses. In some embodiments, the one or more types of viruses includes SARS-CoV-2.

In some embodiments, the electronic device downloads and executes software application instructions that cause the electronic device to register and communicate with the assembly.

In some embodiments, the smart safe body further comprises at least one soundproofing material.

In an embodiment, the smart safe console system includes a control module that is configured to prevent operation of the vehicle unless the safe body is closed and the electronic device is secured within the safe body.

In some embodiments, the assembly communicates with a provider and with the vehicle.

In some embodiments, the button initiates communication with a virtual assistant of the electronic device.

In some embodiments, the provider provides one or more of: phone service, Internet service, or vehicle navigation services.

In some embodiments, the virtual assistant provides vehicle navigation services.

In some embodiments, vehicle navigation services are provided in connection with one or more of: Apple CarPlay® and Android Auto®, preferably where such application is used in connection with the provider or with the virtual assistant.

In an embodiment, the smart safe console system includes a microphone configured to capture a voice of a user.

In some embodiments, the assembly is configured to communicate with an audio system of the vehicle, preferably where the assembly is configured to answer incoming phone calls and provide hands-free phone service by directing communication with the electronic device through the audio system and the microphone.

In some embodiments, the assembly is configured to automatically answer incoming phone calls.

In an embodiment, the smart safe console system includes an override apparatus configured to allow a user to override the control module and permit operation of the vehicle when the electronic device is not secured within the safe body.

The present disclosure also provides a smart safe console system comprising an assembly mounted in a vehicle, the smart safe console system including: a safe body that during vehicle use secures an electronic device against physical access, preferably where the safe body opens and closes, and, when closed, the safe body secures the electronic device against physical access, preferably where the safe body is configured to communicate with the electronic device, when the electronic device is placed within the safe body. In an embodiment, the smart safe console system includes a button that controls input to and output from the electronic device. In an embodiment, the smart safe console system includes a wireless charging apparatus configured to wirelessly charge the electronic device, when the electronic device is placed within the safe body. In an embodiment, the smart safe console system includes a control module that is configured to prevent operation of the vehicle unless the safe body is closed and the electronic device is secured within the safe body. In embodiment, the smart safe console system includes an override apparatus configured to allow a user to override the control module and permit operation of the vehicle when the electronic device is not secured within the safe body.

The claims should not necessarily be construed as limited to addressing any of the particular problems or deficiencies discussed hereinabove. To the accomplishment of the above, this disclosure may be embodied in the form illustrated in the accompanying drawings. Attention is called to the fact, however, that the drawings are illustrative only. Variations are contemplated as being part of the disclosure.

Implementations may include one or a combination of any two or more of the aforementioned features or embodiments.

These and other aspects, features, implementations, and advantages can be expressed as methods, apparatuses, systems, components, program products, business methods, and means or steps for performing functions, or some combination thereof.

Other features, aspects, implementations, and advantages will become apparent from the descriptions, the drawings, and the claims.

DETAILED DESCRIPTION OF THE PREFERRED EMBODIMENTS

Reference will now be made in detail to each embodiment of the present invention. Such embodiments are provided by way of explanation of the present invention, which is not intended to be limited thereto in any manner whatsoever. In fact, those of ordinary skill in the art may appreciate upon reading the present specification and viewing the present drawings that various modifications and variations can be made thereto.

For purposes of the present disclosure of the invention, unless specifically disclaimed, the singular includes the plural and vice-versa, the words "and" and "or" shall be both conjunctive and disjunctive, the words "any" and "all" shall both mean "any and all".

As discussed above, embodiments of the present disclosure relate to containment systems for electronic devices and more particularly to a smart safe console system and method as used to improve vehicle safety while utilizing features on electronic devices.

Generally, the present invention includes a console which may be compatible with a variety of electronic devices such as smart phones, smart watches (iWatches), and smart glasses. The system may be installed in the area between an operator and a passenger, typically called the 'middle console', in any vehicle such as a train, boat, truck, or car. The area between an operator and a passenger may also be a center console armrest in some embodiments. With the electronic devices locked away in the present invention, the operator can manipulate the vehicle with their full attention and any passengers do not have to worry if the operator is texting on the electronic device, on a social media site, or otherwise distracted.

Referring now more specifically to the drawings by numerals of reference, there is shown in FIGS. 1-4, various views of a smart safe console system 100.

FIG. 1 shows smart safe console system 100 during an 'in-use' condition 50, according to an embodiment of the present disclosure. Here, the smart safe console system 100 may be beneficial for use by an operator 40 to improve vehicle safety in relation to the use of electronic devices 21. As illustrated, the smart safe console system 100 may comprise a smart safe console assembly 110 including a smart safe body 1 suitable to house at least one electronic device 21. The electronic device 21 may be able to be isolated from hand-held use by the smart safe body 1.

The smart safe console assembly 110 may also include an engager-button 2 configured for controlling input and output communications to and from the electronic device 21 (e.g., text messages) when a vehicle 45 hosting the smart safe console system 100 is in use. The smart safe console assembly 110 may be in communication with a provider and/or with the vehicle 45 and may be configured to control use of the electronic device 21 in relation to manipulation of the vehicle 45.

The provider may provide cellular-phone-service (e.g., phone carriers), internet service (e.g., wireless communication network) to the electronic device 21. Those with ordinary skill in the art will now appreciate that upon reading this specification and by their understanding the art of communications with the electronic device 21 as described herein, methods of restraining, manipulating, providing, safely limiting will be understood by those knowledgeable in such art.

The vehicle 45 may host the smart safe console system 100 such that the smart safe console assembly 110 may be hardwired to the circuitry of the vehicle 45. The vehicle 45 may provide an energy source (e.g. vehicle battery) for powering the smart safe console system 100. Alternatively, the smart safe console assembly 110 may include a self-contained battery for powering the smart safe console system 100. The smart safe console system 100 may be powered by AC power distributed throughout the smart safe console assembly 110 by a DC power supply (e.g. vehicle battery). Other powering means may be used. Hardwired and non-hardwired versions may be employed.

The smart safe console assembly 110 may be in communication with sensors on the vehicle 45 with the sensors able to sense at least one condition of the vehicle 45. The at least one condition of the vehicle 45 may be measured via a proximity sensor, a motion sensor, a speed sensor, an audio sensor, an impact sensor, or combination thereof. The sensors may provide one or more functions for the smart safe console assembly 110 such as sending an automatically generated message from the electronic device 21 to a desired recipient when the impact sensor is sensed. The impact sensor may indicate that an accident to the vehicle 45 has occurred. The desired recipient can be a family member, friend, or third-party (i.e., police). Sensing means may vary.

The smart safe console system 100 may further comprise at least one cigarette socket 3 along an exterior-portion of the smart safe body 1 configured for communicating and powering one or more external electrical accessories with the smart safe console assembly 110.

Another aspect of the present invention may provide for a software application (SW App) that is hosted on the electronic device 21. The software application may be downloaded on the electronic device's 21 memory and be configured to register and facilitate communication between the electronic device 21 and the smart safe console assembly 110. In some embodiments, the registration includes a verification process between the electronic device 21 and the smart safe console assembly 110, preferably where the smart safe console assembly 110 includes a verification button, when depressed, facilitates the verification process, more preferably where the verification button allows the electronic device 21 to sync with the smart safe console assembly 110. In some embodiments, the registration process and/or verification process includes connecting one or both of the smart safe console assembly 110 and the electronic device 21 to a wireless internet hotspot. In an exemplary embodiment, the smart safe console assembly 110 broadcasts a WIFI hotspot for the electronic device 21 to connect to, preferably where the hotspot is named with a name that indicates its connection to the smart safe console assembly 110. In an exemplary embodiment, the registration and/or verification process includes one or more of the steps of: 1) depressing the verification button on the smart safe console assembly 110; 2) sending a message from the smart safe console assembly 110 to the electronic device 21, using the WIFI hotspot, where the message indicates that the registration and/or verification process has begun, and preferably sets a time limit for response and/or sets a verification code or message that must be sent to the smart safe console assembly to complete registration or verification; 3) sending a verification code or message to the smart safe console assembly, whether digitally using the WIFI hotspot from the electronic device 21, or manually; and 4) depressing the verification button again to complete registration and/or verification. In such embodiments, the smart safe console assembly opens to allow access after the registration and/or verification process is completed.

The operator 40 may register to the software application by a phone number or other known identification means associated with the electronic device 21. The registration process may further include registration of emergency contact information, such as, but not limited to, emergency contact phone numbers, medical information, contact information for physicians or doctors associated with the user, addresses, and others. The software application may be linked to the cellular-phone-service such that the phone number can be stored in a national database operated by the cellular-phone-service. The software application may be in communication with the vehicle 45 hosting the smart safe console system 100 such that one or more operations (e.g., unlocking the vehicle 45, rolling down windows, etc.) can be performed to the vehicle 45 from the software application. Further, the software application may allow for personalization of features equipped with the smart safe console assembly 110. In some embodiments, the smart safe console system 100 communicates specific commands to the software application when the safe is opened, such as a command to remind the user to update the software application and allows the signals containing the update material to communicate with the electronic device 21 while the electronic device 21 is secured within the smart safe console assembly 110. In some embodiment, updating occurs when the electronic device 21 is charging in the smart safe console assembly 110. In other embodiments, updating can occur in the smart safe console assembly 110 when the electronic device 21 is not charging.

According to one embodiment, the smart safe console system 100 may be arranged as a kit 105. In particular, the smart safe console system 100 may further include a set of instructions 107. The instructions 107 may detail functional relationships in relation to the structure of the smart safe console system 100 such that the smart safe console system 100 can be used, maintained, or the like, in a preferred manner.

Figure 2:
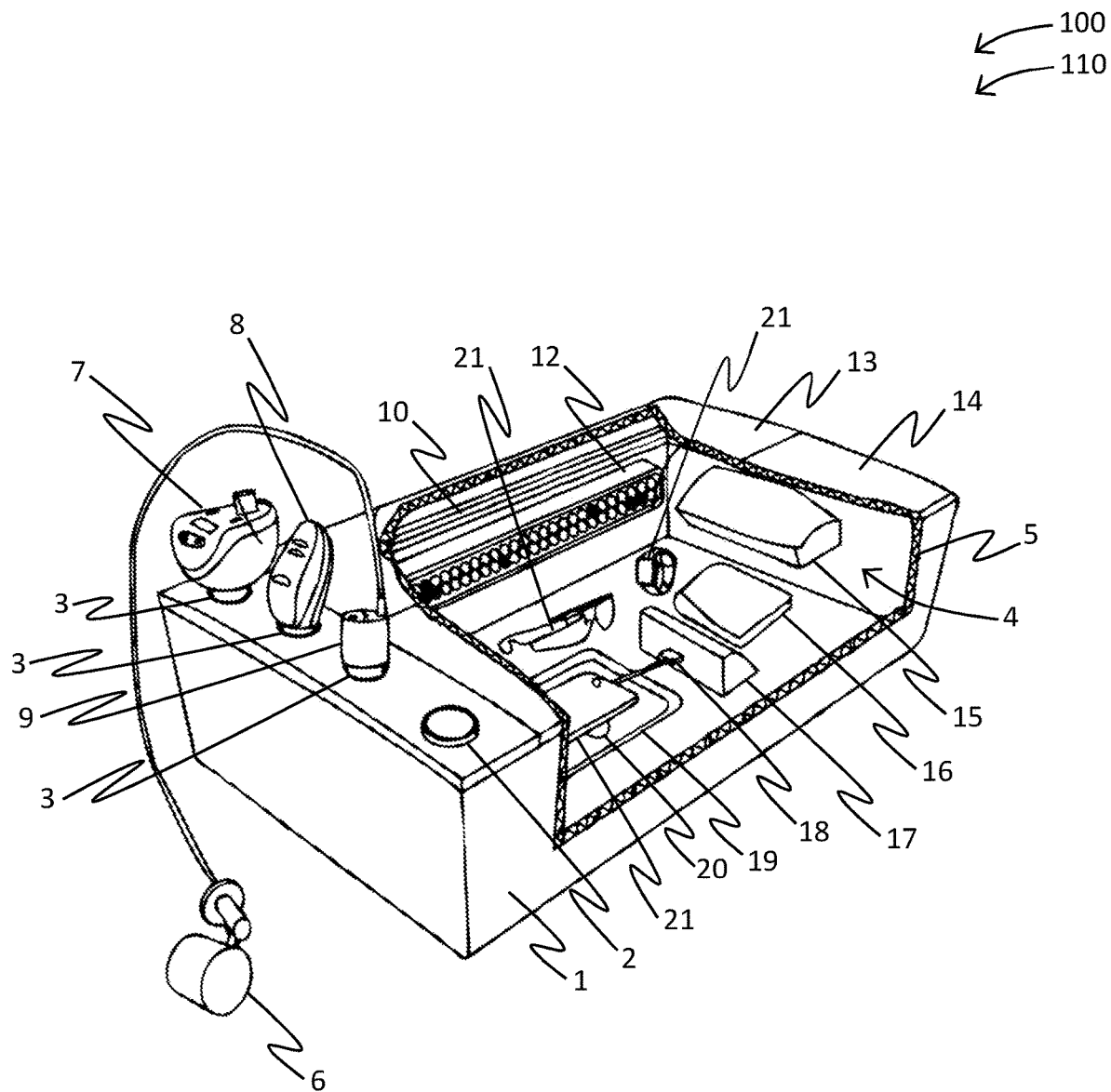

FIG. 2 shows the smart safe console system 100 of FIG. 1, according to an embodiment of the present disclosure. As above, the smart safe console system 100 may include the smart safe console assembly 110 including the smart safe body 1 suitable to house the at least one electronic device 21. The electronic device 21 may be able to be isolated from hand-held use by the smart safe body 1.

The smart safe console assembly 110 may also include the engager-button 2 configured for controlling input and output communications to and from the electronic device 21 when the vehicle 45 hosting the smart safe console system 100 is in use. The smart safe console assembly 110 may be in communication with the provider and with the vehicle 45 and may be configured to control use of the electronic device 21 in relation to manipulation of the vehicle 45. The provider may provide one or more of: cellular-phone-service, internet service, and/or vehicle navigation services, such as those offered through Apple® or Google® as part of Apple Maps® or Google Maps®, to the electronic device 21. The input and output communications may include sending text or voice recorded messages.

The smart safe console assembly 110 may further comprise at least one cigarette socket 3 along the exterior-portion of the smart safe body 1 configured for communicating and powering one or more external electrical accessories with the smart safe console assembly 110. The external electrical accessories include a transmitter 7, a virtual assistant device 9, a fragrance emitter 8, or combination thereof. The at least one cigarette socket 3 may communicably connect to the smart safe console assembly 110 such that the external electrical accessories are in communication with the provider and with the vehicle 45. Each of the external electrical accessories may be connected (with an adapter) or otherwise equipped with a rearward protruding electrode for contacting a powered electrical contact within the cigarette socket 3.

In some embodiments, the smart safe body 1 further includes a left-wing 13 and a right-wing 14 configured to move between an opened-state and a closed-state. In other embodiments, alternate configurations for the smart safe body which allow for such opening and closing are also envisioned, such as a shutter mechanism which slides to move between the opened-state and the closed-state, either from top to bottom, or left to right, in a diaphragm configuration, or any other equivalent means as known in the art. When in the opened-state, the electronic device 21 may be inserted or removed from the smart safe body 1. When in the closed-state, the electronic device 21 may be isolated from hand-held use. The left-wing 13 and the right-wing 14 may include a liner 5. Furthermore, the liner 5 may extend around the entire smart safe body 1. The liner 5 comprises of a sound-proofing material and is configured to dampen and inhibit sounds from the electronic device 21 from reaching the operator 40 of the vehicle 45. Sounds generated from the electronic device 21 may distract the operator 40 unless otherwise dampened.

In some embodiments, the smart safe body 1, and/or the liner 5, may include at least one material with electromagnetic radiation shielding properties. Such electromagnetic shielding properties include, for example, the property of preventing wireless electronic communication with an electronic device placed within the smart safe body. In some embodiments, the electromagnetic shielding properties thus include shielding of one or more of any radio frequencies utilized by electronic devices to communicate, such as, but not limited to, frequency bands associated with the following technological standards: GSM, UMTS, LTE, 5G NR, and CDMA. Such frequency bands may include radio frequencies in the ranges of 800-6000 MHz. In some embodiments, the electromagnetic shielding properties may include shielding any other number of frequencies associated with technologies which electronic devices use to communicate, such as Bluetooth, wireless LAN, RFID, and others.

In some embodiments, the smart safe body 1, and/or the liner 5, may include at least one material with antiviral properties. Such antiviral properties may include, for example, the properties of killing and/or inactivating any viruses and/or virus particles which come into contact with the interior or exterior of the smart safe assembly, preferably in less than 60 minutes, more preferably where at least 99.9999% of such virus is destroyed and/or inactivated. In such embodiments, the material may exhibit its antiviral properties through inducing, either directly or indirectly, the degradation of viral genetic material. Examples of viruses killed and/or inactivated include SARS-CoV-2, any other virus associated with COVID-19, or any other viruses. Exemplary embodiments of the at least one material with electromagnetic shielding properties and/or the at least one material with antiviral properties may be found in U.S. application Ser. No. 16/802,830, entitled "Urethane and Graphene Interior Trim Panel", filed Feb. 27, 2020, the entirety of which is hereby incorporated by reference.

In some embodiments, the smart safe body may include a wireless charging apparatus configured to charge the electronic device, when the electronic device is placed within the safe body. Such wireless charging apparatus may use any such wireless charging technologies for charging electronic devices, such as wireless inductive charging, as may be known in the art. In exemplary embodiments, inductive charging technology standards, such as Qi and/or PMA may be used.

The smart safe body 1 may include an interior-housing 4 defined by one or more walls, the left-wing 13, and the right-wing 14. The smart safe body 1 can be provided in a variety of shapes and sizes that fit in the vehicle 45. For example, the smart safe body 1 may include a curved surface on one or more walls or be substantially rectangular/squared. The interior-housing 4 may be equipped with an apparatus configured to emit sanitizing radiation, such as ultraviolet light, into the interior of the safe body, when the safe body is closed. In an exemplary embodiment, the interior-housing 4 may be equipped with an ultraviolet light disinfecting device 12 configured to destroy and/or inactivate one or more of: bacteria, viruses, yeast, or other pathogens, on one or more surfaces housed within the smart safe body 1. In an exemplary embodiment, the sanitizing radiation emitted by the apparatus is sufficient to destroy or inactivate SARS-CoV-2. The interior-housing 4 may further be equipped with a sunglasses holder 15, a wallet holder 16, a charging unit 17, a docking station 19, an electromagnetic field (EMF) battery 20, colored LED light strips 10, or combination thereof. The colored LED light strips 10 may be customized (i.e., changing of light colors) via the SW App. Additionally, other features may be equipped in the interior-housing not shown in FIG. 2, such as a cooling fan, when desired.

Figure 3:
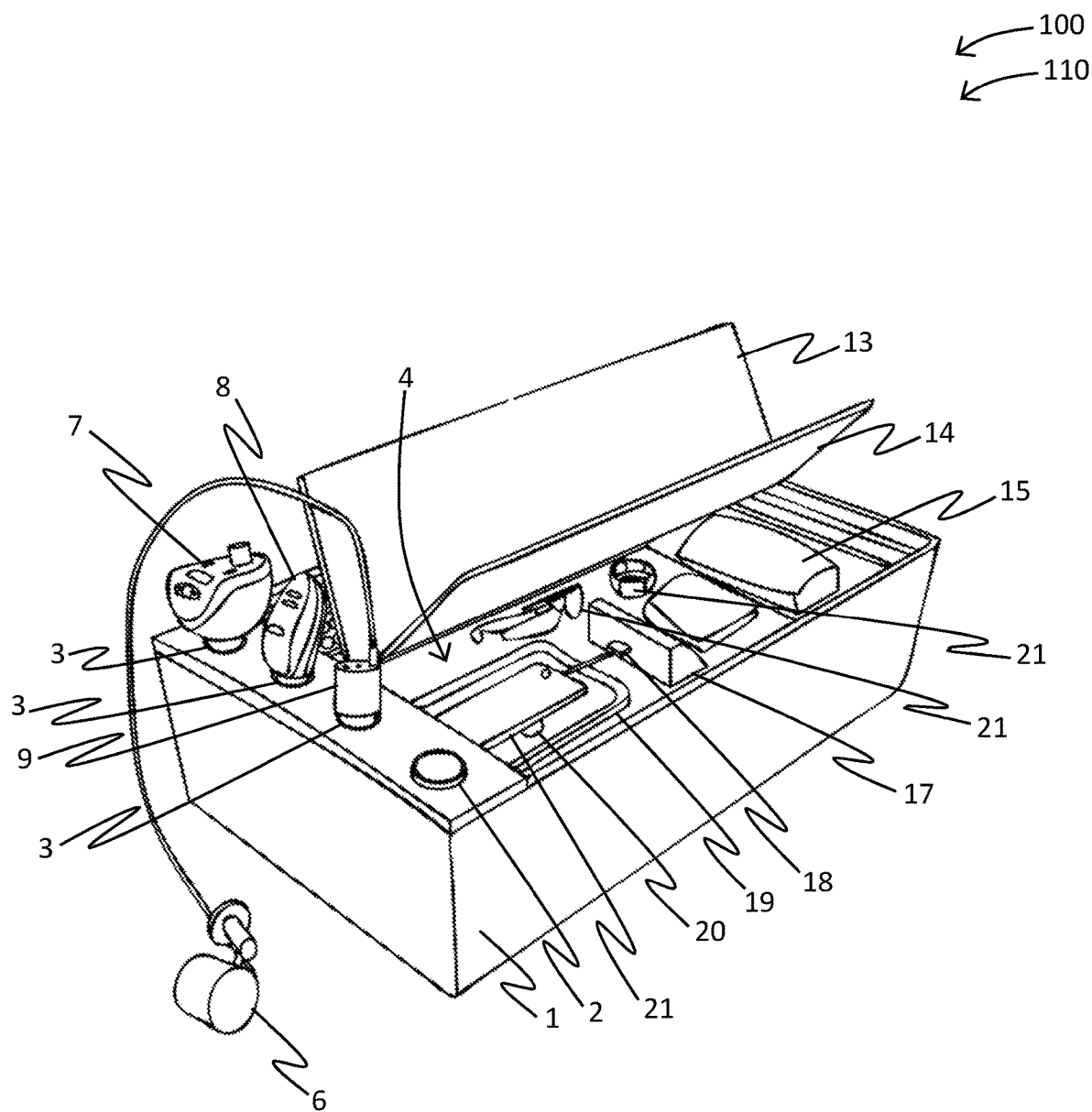

FIG. 3 is a perspective view of the smart safe console system 100 of FIG. 1, according to an embodiment of the present disclosure. As noted above, the smart safe body 1 includes the left-wing 13 and the right-wing 14 configured to move between the opened-state and the closed-state. When in the opened-state, the electronic device 21 may be inserted or removed from the smart safe body 1. When in the closed-state, the electronic device 21 may be isolated from hand-held use. The left-wing 13 and the right-wing 14 may open on opposite sides (as shown) or they may open on the same side.

The smart safe body 1 may further include the interior-housing 4 defined by one or more walls, the left-wing 13, and the right-wing 14. The interior-housing 4 may be equipped with the charging unit 17 including an electrical connector 18 (e.g., USB socket and/or plug) for connecting the electronic device 21 to be charged, and the docking station 19 for holding the electronic device 21 proximate the charging unit 17 and the electrical connector 18. The interior-housing 4 may further be equipped with the electromagnetic field (EMF) battery 20 positioned below the docking station 19 and is configured prevent radiation from emitting from the electronic device 21 when housed within the smart safe body 1.

The smart safe assembly 110 may be in communication with a control module configured to permit non-operation of the vehicle 45 when the electronic device 21 is not in a sensed-condition, and operation of the vehicle 45 when the electronic device 21 is in the sensed-condition. The sensed-condition may be when the electronic device 21 is electrically connected to the charging unit 17, and the left-wing 13 and the right-wing 14 is in the closed-state. The charging unit 17, and the left-wing 13 and the right-wing 14 may include at least one operation sensor coupled to the control module. The at least one operation sensor may be configured to detect the sensed-condition and send to the control module upon receipt of the sensed-condition. It should be noted that the electronic device 21 may be required to be registered with the software application prior to receipt of the sensed-condition such that all electronic devices 21 can be accounted for.

Figure 4:
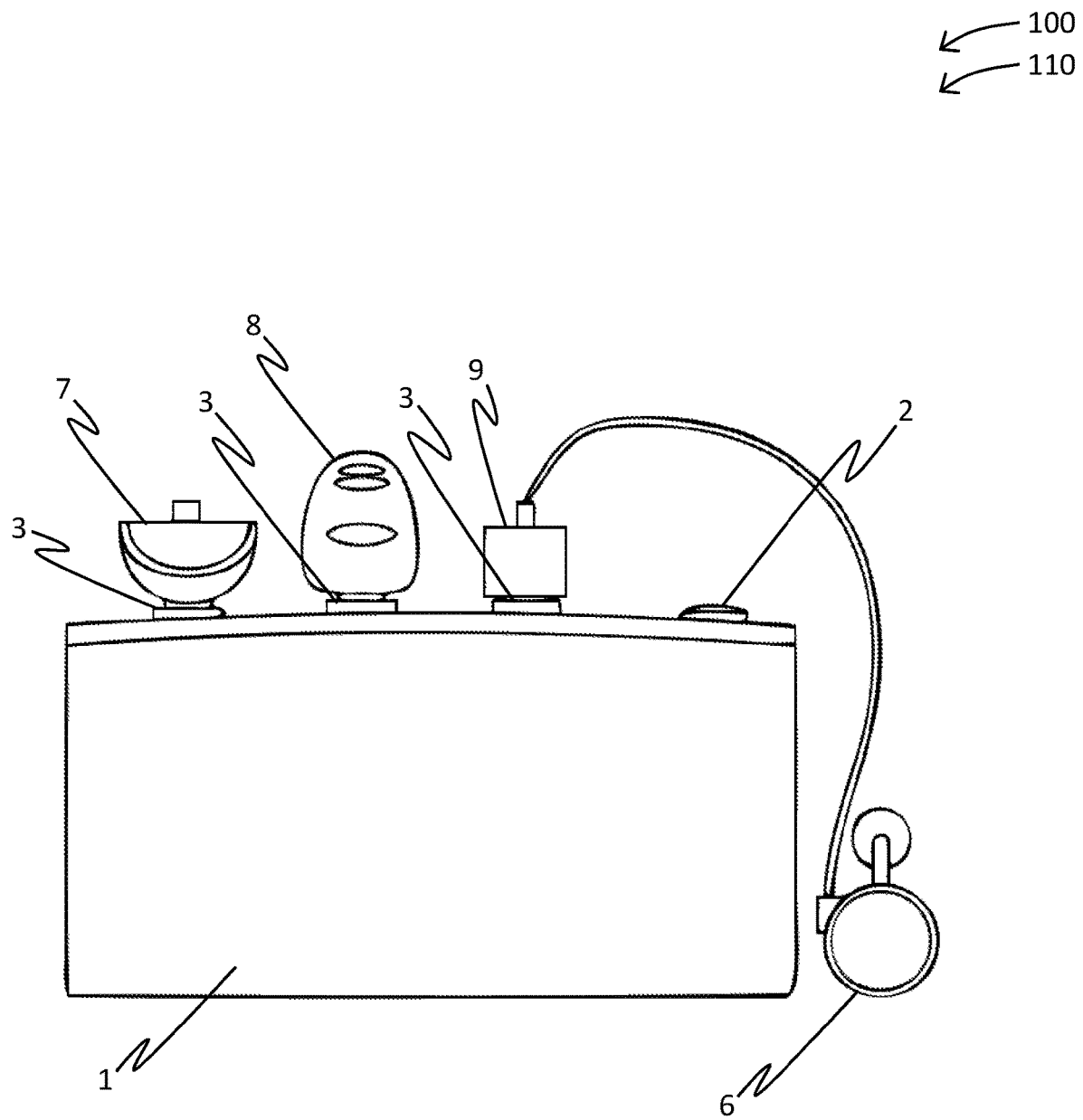

FIG. 4 is a front view of the smart safe console system 100 of FIG. 1, according to an embodiment of the present disclosure. The smart safe console assembly 110 may comprise the at least one cigarette socket 3 along the exterior-portion of the smart safe body 1 configured for communicating and powering the one or more external electrical accessories with the smart safe console assembly 110. The external electrical accessories may include the transmitter 7, the virtual assistant device 9, and the fragrance emitter 8. The fragrance emitter 8 may be configured to emit one or more scents within the vehicle 45. The fragrance emitter 8 may continually emit scents or periodically on a timer. Other features may be included.

In some embodiments, the virtual assistant may be hosted entirely on the smart safe assembly or on the electronic device itself. However, in other embodiments, the virtual assistant may be hosted in a separate device. The virtual assistant device 9 may be in communication with the electronic device 21 (hosting the software application) and the engager-button 2 and is configured to enable voice input communication and voice output communication between the virtual assistant device 9 and the electronic device 21 when a signal is received from the engager-button 2. Commonly known virtual assistant devices 9 include AMAZON ECHO, ALEXA, and GOOGLE ASSISTANT all of which may be pre-equipped with one or more speaker(s) and microphone(s) to enable the voice input communication and the voice output communication. The voice input communication and the voice output communication may include asking and receiving information ranging from the weather report to any encyclopedia question. Further, the operator 40 may personalize the voice input communication and the voice output communication via the virtual assistant device 9 to provide voices to be male, female, celebrity, and the like. The virtual assistant device 9 may include a cord and a suction cup 6 such that the virtual assistant device 9 can be fastened to the windshield of the vehicle 45.

The virtual assistant may be in communication with a navigational system (e.g., GARMIN technology) hosted in the vehicle 45 and/or with the electronic device 21. This way the electronic device 21 can remain in the smart safe body 1 while the operator 40 uses this technology for navigation. The operator 40 of the vehicle 45 can engage the engager-button 2 to provide voice input communication. The voice input communication may provide one or more services to the operator 40 such as but not limited to voice recorded messages processed on the virtual assistant to send to the desired recipient via the cellular-phone-service (e.g., notifying the desired recipient when the operator 40 is unable to respond due to driving and/or approximate times when the operator 40 will be free to respond based on communications received by the navigational system), purchasing of one or more items via the internet service, requesting a list of songs played on the radio, inputting personal information associated with the operator 40 to be stored on the electronic device 21, requesting specific responses based on the inputted personal information (i.e. bank account information), etc. The voice output communication may provide one or more services to the operator 40 such as reminders from the calendar on the electronic device 21, reminders for ongoing conversations on the electronic device 21, automatic updates for the electronic device 21, responses to the voice input communication, and the like. The virtual assistant may provide vehicle navigational services itself, or other vehicle utilities, preferably through compatibility through third-party applications, although the use of proprietary software is also contemplated. Examples of such vehicle navigational applications or vehicle utility applications intended to be compatible with the virtual assistant include any driving or navigational application provided by Apple® or Google®, such as Apple Maps®, Apple CarPlay®, or Google Maps®, MirrorLink®, Drivemode®, Cardo®, Android Auto®, navigational systems offered by Airbiquity® or Orderwerks®, JBL Smartbase® associated applications, Car dashdroid-Car Infotainment®, CARFAX Car Care®, Cycle®, Driver®, Fully®, HONK Partn®, and any others.

In some embodiments, the smart safe console system includes a microphone configured to capture a voice of the user. Such voice capture may be used to interact with one or more of the features of the smart safe console system, through voice recognition software, or other means. In some embodiments, the smart safe console system assembly is configured to communicate with an audio system of the vehicle. Such communication with the audio system of the vehicle may be used for, amongst other functions, communicating alerts or other information to the user, or providing audio functions of the smart safe console system, such as music players, or hands-free call answering. In an exemplary embodiment, the assembly is configured to answer incoming phone calls, preferably through manual means such as pushing a button, more preferably through voice activated means, by using the microphone, and even more preferably by having the assembly automatically answer calls, and provide hands-free phone service by directing communication with the electronic device through the audio system and the microphone.

The transmitter 7 may be configured to communicate with a controller and a processor. The software application may be programmed to include a switch that enables communication between the transmitter 7 and the controller and the processor. The switch may be manually activated via interfacing with the software application or activated once the navigational system equipped on the vehicle 45 receives a signal that the desired destination (e.g., home) is less than a predetermined distance away. The controller and the processor may be communicably coupled to one or more features within the desired destination such that the one or more features can be turned on/off. The one or more features may include but not be limited to an alarm system, temperature settings, propane fireplace, lighting, sound system, such as a stereo, and powered kitchen accessories. Those with ordinary skill in the art will now appreciate that upon reading this specification and by their understanding the art of transmitters as described herein, methods of communication with powered objects via the transmitter 7 will be understood by those knowledgeable in such art.

Figure 5:
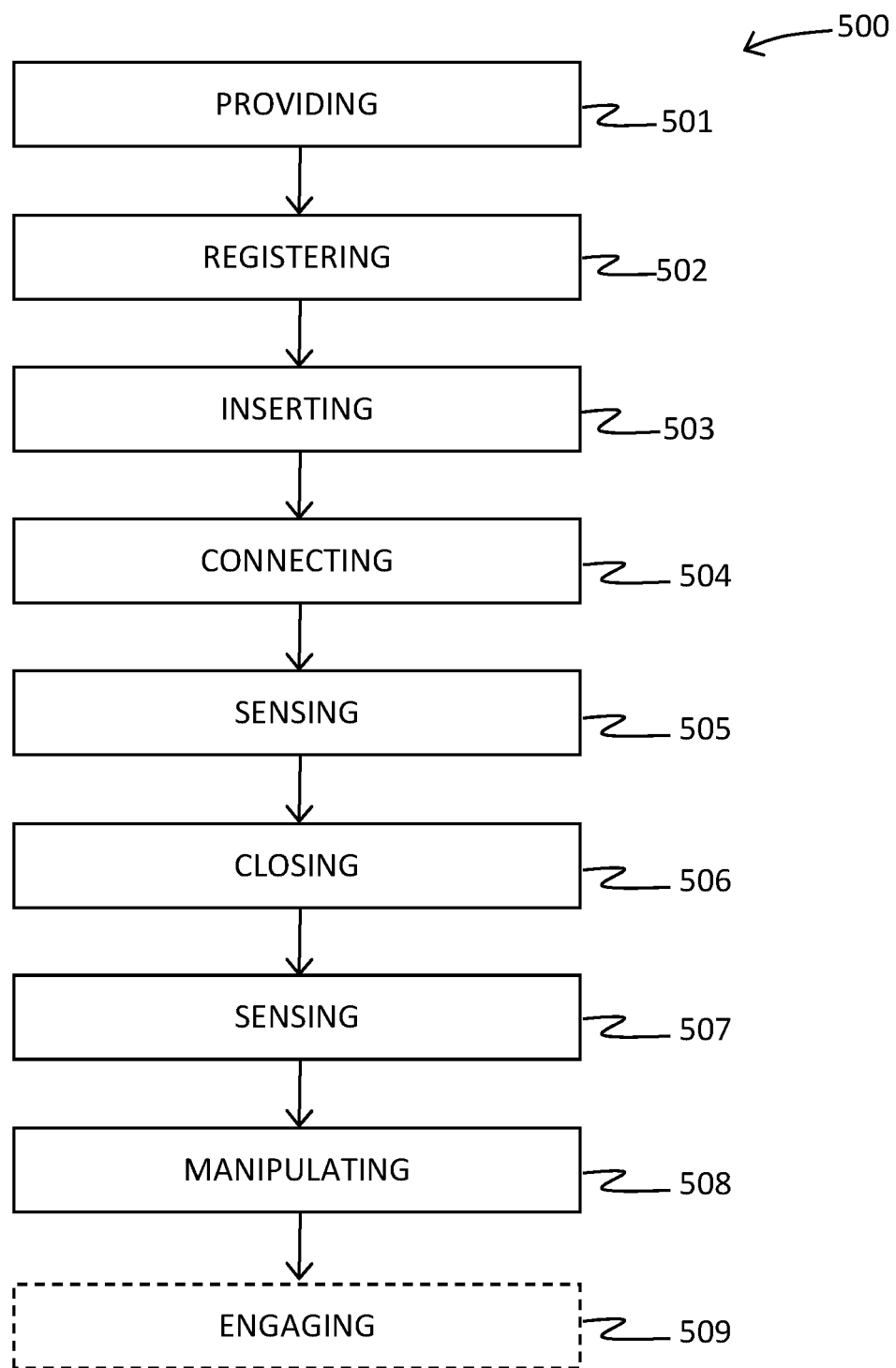

FIG. 5 is a flow diagram illustrating a method for using a smart safe console system 500, according to an embodiment of the present disclosure. In particular, the method for using the smart safe console system 500 may include one or more components or features of the smart safe console system 100 as described above. As illustrated, the method for using the smart safe console system 500 may include the steps of: step one 501, providing a smart safe console assembly 110 including a smart safe body 1 suitable to house at least one electronic device 21, an engager-button 2 configured for controlling input and output communications to and from the electronic device 21 when a vehicle 45 hosting the smart safe console system 100 is in use; the smart safe body 1 further includes a left-wing 13 and a right-wing 14 configured to move between an opened-state and a closed-state, and an interior-housing 4 defined by one or more walls, the left-wing 13, and the right-wing 14; the smart safe console assembly 110 may be in communication with a provider and with the vehicle 45 and may be configured to control use of the electronic device 21 in relation to manipulation of the vehicle 45; step two 502, registering the electronic device 21 with a software application in communication with the smart safe assembly 110; step three 503, inserting the electronic device 21 into the smart safe body 1; step four 504, connecting the electronic device 21 to a charging unit 17 equipped in the interior-housing 4; step five 505, sensing the electronic device 21 is connected to the charging unit 17 via at least one operation sensor and registered with the software application; step six 506, closing the left-wing 13 and the right-wing 14; step seven 507, sensing the left-wing 13 and the right-wing 14 are in the closed-state via the at least one operation sensor; step eight 508, manipulating the vehicle 45 (e.g., turning the vehicle 45 on); and step nine 509, engaging the engager-button 2 for controlling the input and the output communications to and from the electronic device 21.

It should be noted that step nine 509 is an optional step and may not be implemented in all cases. Optional steps of method of use 500 are illustrated using dotted lines in FIG. 5 so as to distinguish them from the other steps of method of use 500. It should also be noted that the steps described in the method of use can be carried out in many different orders according to user preference. The use of "step of" should not be interpreted as "step for", in the claims herein and is not intended to invoke the provisions of 35 U.S.C. § 112(f). It should also be noted that, under appropriate circumstances, considering such issues as design preference, user preferences, marketing preferences, cost, structural requirements, available materials, technological advances, etc., other methods for using the smart safe console system 100 (NOTE: e.g., different step orders within above-mentioned list, elimination or addition of certain steps, including or excluding certain maintenance steps, etc.), are taught herein.

In some embodiments, the smart safe console system may be a before-market product for vehicles. In some embodiments, the smart safe console system may be an after-market product for vehicles. In many embodiments, the smart safe console system may be made with many different dimensions and/or shapes, or is adjustable in its dimensions and/or shapes, so as to properly fit many different shapes, sizes, and makes of various vehicles and the various middle consoles or center armrests that are in such vehicles.

In some embodiments, the smart safe console system includes an override apparatus configured to allow a user to override the control module and permit operation of the vehicle, preferably when the electronic device is not secured within the safe body, or regardless of whether the electronic device is secured within the safe body or not. In some embodiments, the override apparatus may be configured to require the user to enter information used to verify the user's identity before the override apparatus will override the control module. In some embodiments, the override apparatus may be configured to include a function to notify an external user, such as an administrator, that override of the control module is requested, and will not override the control module until such request is granted by the external user. In some embodiments, the override apparatus directly overrides the control module. In some embodiments, the override apparatus may provide the user with a manual means of overriding the control module, such as a specialized key or other type of tool or tools. In a preferable embodiment, the manual means of overriding the control module includes a specialized key, and the smart safe assembly includes a keyhole corresponding to the specialized key. In an exemplary embodiment, the keyhole on the smart safe assembly is hidden behind an override button, the override button configured such that when depressed, opens to reveal the keyhole. In some embodiments, when the override button is depressed, the override apparatus is engaged, and the keyhole is only revealed once the override apparatus verifies the user's identity. In some embodiments, the override key is contained in a compartment, and is only provided to the user once the override apparatus verifies the user's identity. In some embodiments, further steps are required to enable either the override apparatus to override the control module, or to reveal the override key, such as requiring the user to use a specialized tool, such as a screwdriver, to remove certain screws and/or caps located on positions on the smart safe assembly and/or inside the center console armrest. In some embodiments, the override apparatus only overrides the control module once the override key is inserted into the keyhole and turned. In some embodiments, the smart safe console system includes an emergency button, which when depressed for a predetermined amount of time will notify the authorities, such as the police, of the vehicle's location, preferably with a request for assistance.

It is understood that when an element is referred hereinabove as being "on" another element, it can be directly on the other element or intervening elements may be present therebetween. In contrast, when an element is referred to as being "directly on" another element, there are no intervening elements present.

Moreover, any components or materials can be formed from a same, structurally continuous piece or separately fabricated and connected.

It is further understood that, although ordinal terms, such as, "first," "second," and "third," are used herein to describe various elements, components, regions, layers and/or sections, these elements, components, regions, layers and/or sections should not be limited by these terms. These terms are only used to distinguish one element, component, region, layer and/or section from another element, component, region, layer and/or section. Thus, a "first element," "component," "region," "layer" and/or "section" discussed below could be termed a second element, component, region, layer and/or section without departing from the teachings herein.

Features illustrated or described as part of one embodiment can be used with another embodiment and such variations come within the scope of the appended claims and their equivalents. Implementations may also include one or a combination of any two or more of the aforementioned features or embodiments.

Spatially relative terms, such as "beneath," "below," "lower," "above," "upper" and the like, are used herein for ease of description to describe one element or feature's relationship to another element(s) or feature(s) as illustrated in the figures. It is understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device can be otherwise oriented (rotated 90 degrees or at other orientations) and the spatially relative descriptors used herein interpreted accordingly.

Example embodiments are described herein with reference to cross section illustrations that are schematic illustrations of idealized embodiments. As such, variations from the shapes of the illustrations, for example, of manufacturing techniques and/or tolerances, are to be expected. Thus, example embodiments described herein should not be construed as limited to the particular shapes of regions as illustrated herein, but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

As the invention has been described in connection with what is presently considered to be the most practical and various embodiments, it is to be understood that the invention is not to be limited to the disclosed embodiments, but on the contrary, is intended to cover various modifications and equivalent arrangements included within the scope of the appended claims. Although specific terms are employed herein, they are used in a generic and descriptive sense only and not for purposes of limitation.

This written description uses examples to disclose the invention, including the best mode, and also to enable any person skilled in the art to practice the invention, including making and using any devices or systems and performing any incorporated methods. The patentable scope of the invention is defined in the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The claims should not necessarily be construed as limited to addressing any of the particular problems or deficiencies discussed hereinabove. To the accomplishment of the above, this disclosure may be embodied in the form illustrated in the accompanying drawings. Attention is called to the fact, however, that the drawings are illustrative only. Variations are contemplated as being part of the disclosure.

In conclusion, herein is presented a device for supporting a torso of a user and a method of use thereof. The disclosure is illustrated throughout the written description. It should be understood that numerous variations are possible while adhering to the inventive concept. Such variations are contemplated as being a part of the present disclosure.

What is claimed is:

1. A smart safe console system comprising an assembly mounted in a vehicle, the smart safe console system including:
   a safe body that during vehicle use secures an electronic device against physical access,
      wherein the safe body opens and closes, and, when closed, the safe body secures the electronic device against physical access,
      wherein the safe body is configured to communicate with the electronic device, when the electronic device is placed within the safe body,
      wherein the safe body comprises at least one material with electromagnetic radiation shielding properties, and
      wherein the safe body comprises at least one material with antiviral properties;
   a button that controls input to and output from the electronic device; and
   a wireless charging apparatus configured to wirelessly charge the electronic device, when the electronic device is placed within the safe body.

2. The smart safe console system of claim 1, further including an apparatus configured to emit sanitizing radiation into the interior of the safe body, when the safe body is closed.

3. The smart safe console system of claim 2, wherein the emitted sanitizing radiation is ultraviolet radiation sufficient to inactivate or destroy one or more types of viruses.

4. The smart safe console system of claim 3, wherein the one or more types of viruses includes SARS-COV-2.

5. The smart safe console system of claim 1, wherein the electronic device downloads and executes software application instructions that cause the electronic device to register and communicate with the assembly.

6. The smart safe console system of claim 1, wherein the smart safe body further comprises at least one soundproofing material.

7. The smart safe console system of claim 1, further comprising a control module that is configured to prevent operation of the vehicle unless the safe body is closed and the electronic device is secured within the safe body.

8. The smart safe console system of claim 1, wherein the assembly communicates with a provider and with the vehicle.

9. The smart safe console system of claim 1, wherein the button initiates communication with a virtual assistant of the electronic device.

10. The smart safe console system of claim 8, wherein the provider provides one or more of: phone service, Internet service, or vehicle navigation services.

11. The smart safe console system of claim 9, wherein the virtual assistant provides vehicle navigation services.

12. The smart safe console system of claim 8, further comprising a microphone configured to capture a voice of a user.

13. The smart safe console system of claim 12, wherein the assembly is configured to communicate with an audio system of the vehicle, and wherein the assembly is configured to answer incoming phone calls and provide hands-free phone service by directing communication with the electronic device through the audio system and the microphone.

14. The smart safe console system of claim 13, wherein the assembly is configured to automatically answer incoming phone calls.

15. The smart safe console system of claim 7, further comprising an override apparatus configured to allow a user to override the control module and permit operation of the vehicle when the electronic device is not secured within the safe body.

16. The smart safe console system of claim 10, wherein the provider provides vehicle navigation services in connection with one or more of: Apple CarPlay® and Android Auto®.

17. The smart safe console system of claim 11, wherein the virtual assistant provides vehicle navigation services in connection with one or more of: Apple CarPlay® and Android Auto®.

18. A smart safe console system comprising an assembly mounted in a vehicle, the smart safe console system including:
   a safe body that during vehicle use secures an electronic device against physical access,
      wherein the safe body opens and closes, and, when closed, the safe body secures the electronic device against physical access,
      wherein the safe body is configured to communicate with the electronic device, when the electronic device is placed within the safe body,
      wherein the safe body comprises at least one material with electromagnetic radiation shielding properties,
   a wireless charging apparatus configured to wirelessly charge the electronic device, when the electronic device is placed within the safe body;
   a control module that is configured to prevent operation of the vehicle unless the safe body is closed and the electronic device is secured within the safe body; and
   an override apparatus configured to allow a user to override the control module and permit operation of the vehicle when the electronic device is not secured within the safe body.

* * * * *